(12) United States Patent
Reiss et al.

(10) Patent No.: US 6,582,394 B1
(45) Date of Patent: Jun. 24, 2003

(54) STENT AND CATHETER ASSEMBLY AND METHOD FOR TREATING BIFURCATED VESSELS

(75) Inventors: Paul Reiss, Santa Clara, CA (US); Mary Dennehy, Pleasanton, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 72 days.

(21) Appl. No.: 09/713,648

(22) Filed: Nov. 14, 2000

(51) Int. Cl.$^7$ .............................................. A61M 29/00
(52) U.S. Cl. .............................. 604/96.01; 604/103.05; 623/1.15
(58) Field of Search ...................... 623/1.15; 604/96.01, 604/103.05

(56) References Cited

U.S. PATENT DOCUMENTS

| | | |
|---|---|---|
| 2,845,959 A | 8/1958 | Sidebotham |
| 2,978,787 A | 4/1961 | Liebig |
| 2,990,605 A | 7/1961 | Demsyk |
| 3,029,819 A | 4/1962 | Starks |
| 3,096,560 A | 7/1963 | Liebig |
| 3,142,067 A | 7/1964 | Liebig |
| 3,397,699 A | 8/1968 | Kohl |
| 3,908,662 A | 9/1975 | Razgulov et al. |
| 3,945,052 A | 3/1976 | Liebig |
| 4,041,931 A | 8/1977 | Elliott et al. |

(List continued on next page.)

FOREIGN PATENT DOCUMENTS

| | | |
|---|---|---|
| EP | 0 461 791 A1 | 12/1991 |
| EP | 0 466 518 A3 | 1/1992 |
| EP | 0 747 020 A2 | 12/1996 |
| EP | 0 804 907 A2 | 11/1997 |
| EP | 0 884 028 A1 | 12/1998 |
| EP | 0 965 311 A2 | 12/1999 |
| FR | 2 673 843 A1 | 9/1992 |
| FR | 2 737 969 A1 | 2/1997 |
| FR | 2 740 346 A1 | 4/1997 |
| SU | 1217402 A | 3/1986 |

(List continued on next page.)

OTHER PUBLICATIONS

International Application Published Under the Patent Cooperation Treaty (PCT) as Publication No. WO 00/71054 A1 to Applicant Conor Medsystems, Inc., published Nov. 30, 2000.

Lawrence, David D., Jr., M.D., et al., *Percutaneous Endovascular Graft: Experimental Evaluation*, Radiology, vol. 163, No. 2, pp. 357–360 (1987).

Yoshioka, Tetsuya, et a., *Self–Expanding Endovascular Graft: An Experimental Study in Dogs*, Radiology, vol. 170, pp. 1033–1037 (1989).

(List continued on next page.)

*Primary Examiner*—Ronald Capossela
(74) *Attorney, Agent, or Firm*—Fulwider Patton Lee & Utecht, LLP

(57) ABSTRACT

An apparatus and method is provided for stenting bifurcated vessels. A main-vessel stent and delivery system is provided for implanting a stent in the main vessel of a bifurcated vessel, wherein the main-vessel stent has an aperture bordered by closed stent cells that aligns with the opening to a side-branch vessel to permit substantially unobstructed blood flow between the main vessel and the side-branch vessel. The delivery system includes a catheter assembly having distal and proximal balloons separated by a positioning guide wire exit port located at the distal end of the catheter. The catheter assembly is advanced over a pair of guide wires for delivering, appropriately orienting, and implanting the main-vessel stent.

7 Claims, 10 Drawing Sheets

U.S. PATENT DOCUMENTS

| | | | |
|---|---|---|---|
| 4,047,252 A | 9/1977 | Liebig et al. | |
| 4,061,134 A | 12/1977 | Samuels et al. | |
| 4,108,161 A | 8/1978 | Samuels et al. | |
| 4,140,126 A | 2/1979 | Choudhury | |
| 4,193,137 A | 3/1980 | Heck | |
| 4,202,349 A | 5/1980 | Jones | |
| 4,214,587 A | 7/1980 | Sakura, Jr. | |
| 4,517,687 A | 5/1985 | Liebig et al. | |
| 4,560,374 A | 12/1985 | Hammerslag | |
| 4,562,596 A | 1/1986 | Kornberg | |
| 4,577,631 A | 3/1986 | Kreamer | |
| 4,617,932 A | 10/1986 | Kornberg | |
| 4,652,263 A | 3/1987 | Herweck et al. | |
| 4,693,249 A | 9/1987 | Schenck et al. | |
| 4,728,328 A | 3/1988 | Hughes et al. | |
| 4,732,152 A | 3/1988 | Wallsten et al. | |
| 4,787,899 A | 11/1988 | Lazarus | |
| 4,793,348 A | 12/1988 | Palmaz | |
| 4,795,458 A | 1/1989 | Regan | |
| 4,795,465 A | 1/1989 | Marten | |
| 4,830,003 A | 5/1989 | Wolff et al. | |
| 4,872,874 A | 10/1989 | Taheri | |
| 4,878,906 A | 11/1989 | Lindemann et al. | |
| 4,892,539 A | 1/1990 | Koch | |
| 4,969,896 A | 11/1990 | Shors | |
| 4,994,071 A | 2/1991 | MacGregor | |
| 5,026,377 A | 6/1991 | Burton et al. | |
| 5,047,050 A | 9/1991 | Arpesani | |
| 5,064,435 A | 11/1991 | Porter | |
| 5,104,399 A | 4/1992 | Lazarus | |
| 5,108,424 A | 4/1992 | Hoffmann, Jr. et al. | |
| 5,127,919 A | 7/1992 | Ibrahim et al. | |
| 5,156,619 A | 10/1992 | Ehrenfeld | |
| 5,178,630 A | 1/1993 | Schmitt | |
| 5,178,634 A | 1/1993 | Ramos Martinez | |
| 5,197,976 A | 3/1993 | Herweck et al. | |
| 5,197,977 A | 3/1993 | Hoffman, Jr. et al. | |
| 5,197,978 A | 3/1993 | Hess | |
| 5,222,971 A | 6/1993 | Willard et al. | |
| 5,226,913 A | 7/1993 | Pinchuk | |
| 5,234,457 A | 8/1993 | Andersen | |
| 5,304,220 A | 4/1994 | Maginot | |
| 5,316,023 A | 5/1994 | Palmaz et al. | |
| 5,360,443 A | 11/1994 | Barone et al. | |
| 5,413,581 A | 5/1995 | Goy | |
| 5,443,497 A | 8/1995 | Venbrux | |
| 5,443,498 A | 8/1995 | Fontaine | |
| 5,456,712 A | 10/1995 | Maginot | |
| 5,507,769 A | 4/1996 | Marin et al. | |
| 5,522,880 A | 6/1996 | Baron et al. | |
| 5,527,355 A | 6/1996 | Ahn | |
| 5,562,724 A | 10/1996 | Vorwerk et al. | |
| 5,562,726 A | 10/1996 | Chuter | |
| D376,011 S | 11/1996 | Nunokawa | |
| 5,571,167 A | 11/1996 | Maginot | |
| 5,571,170 A | 11/1996 | Palmaz et al. | |
| 5,571,171 A | 11/1996 | Barone et al. | |
| 5,571,173 A | 11/1996 | Parodi | |
| 5,575,817 A | 11/1996 | Martin | |
| 5,578,071 A | 11/1996 | Parodi | |
| 5,578,072 A | 11/1996 | Barone et al. | |
| 5,591,229 A | 1/1997 | Parodi | |
| 5,603,721 A | 2/1997 | Lau et al. | |
| 5,607,444 A | 3/1997 | Lam | |
| 5,609,627 A | 3/1997 | Goicoechea et al. | |
| 5,613,980 A | 3/1997 | Chauhan | |
| 5,617,878 A | 4/1997 | Taheri | |
| 5,628,783 A | 5/1997 | Quiachon et al. | |
| 5,632,763 A | 5/1997 | Glastra | |
| 5,632,772 A | 5/1997 | Alcime et al. | |
| 5,639,278 A | 6/1997 | Dereume et al. | |
| 5,643,340 A | 7/1997 | Nunokawa | |
| 5,669,924 A | 9/1997 | Shaknovich | |
| 5,676,696 A | 10/1997 | Marcade | |
| 5,676,697 A | 10/1997 | McDonald | |
| 5,683,450 A | 11/1997 | Goicoechea et al. | |
| 5,683,452 A | 11/1997 | Barone et al. | |
| 5,683,453 A | 11/1997 | Palmaz | |
| 5,693,084 A | 12/1997 | Chuter | |
| 5,693,086 A | 12/1997 | Goicoechea et al. | |
| 5,693,087 A | 12/1997 | Parodi | |
| 5,693,088 A | 12/1997 | Lazarus | |
| 5,695,517 A | 12/1997 | Marin et al. | |
| 5,709,713 A | 1/1998 | Evans et al. | |
| 5,713,917 A | 2/1998 | Leonhardt et al. | |
| 5,718,724 A | 2/1998 | Goicoechea et al. | |
| 5,720,735 A | 2/1998 | Dorros | |
| 5,743,875 A | 4/1998 | Sirhan et al. | |
| 5,749,825 A | 5/1998 | Fischell et al. | |
| 5,749,888 A | 5/1998 | Yock | |
| 5,755,734 A | 5/1998 | Richter et al. | |
| 5,755,735 A | 5/1998 | Richter et al. | |
| 5,755,771 A | 5/1998 | Penn et al. | |
| 5,766,710 A * | 6/1998 | Turnlund et al. | 428/36.1 |
| 5,776,180 A | 7/1998 | Goicoechea et al. | |
| 5,782,906 A | 7/1998 | Marshall et al. | |
| 5,800,508 A | 9/1998 | Goicoechea et al. | |
| 5,800,520 A | 9/1998 | Fogarty et al. | |
| 5,827,320 A | 10/1998 | Richter et al. | |
| 5,855,600 A | 1/1999 | Alt | |
| 5,871,536 A | 2/1999 | Lazarus | |
| 5,893,887 A | 4/1999 | Jayaraman | |
| 5,895,407 A | 4/1999 | Jayaraman | |
| 5,916,234 A | 6/1999 | Lam | |
| 5,916,263 A | 6/1999 | Goicoechea et al. | |
| 5,919,225 A | 7/1999 | Lau et al. | |
| 5,921,995 A | 7/1999 | Kleshinski | |
| 5,938,696 A | 8/1999 | Goicoechea et al. | |
| 5,954,693 A | 9/1999 | Barry | |
| 5,972,017 A | 10/1999 | Berg et al. | |
| 5,976,155 A | 11/1999 | Foreman et al. | |
| 6,001,124 A | 12/1999 | Bachinski | |
| 6,030,413 A | 2/2000 | Lazarus | |
| 6,030,414 A | 2/2000 | Taheri | |
| 6,030,415 A | 2/2000 | Chuter | |
| 6,033,434 A | 3/2000 | Borghi | |
| 6,033,435 A | 3/2000 | Penn et al. | |
| 6,039,754 A | 3/2000 | Caro | |
| 6,048,361 A | 4/2000 | Von Oepen | |
| 6,051,020 A | 4/2000 | Goicoechea et al. | |
| 6,056,775 A | 5/2000 | Borghi et al. | |
| 6,090,133 A | 7/2000 | Richter et al. | |
| 6,096,071 A * | 8/2000 | Yadav | 623/1.15 |
| 6,096,073 A | 8/2000 | Webster et al. | |
| 6,099,560 A | 8/2000 | Penn et al. | |
| 6,099,597 A | 8/2000 | Adams et al. | |
| 6,117,117 A | 9/2000 | Mauch | |
| 6,129,738 A | 10/2000 | Lashinski et al. | |
| 6,165,195 A | 12/2000 | Wilson | |
| 6,210,429 B1 * | 4/2001 | Vardi et al. | 623/1.11 |

FOREIGN PATENT DOCUMENTS

| | | |
|---|---|---|
| SU | 1318235 A1 | 6/1987 |
| SU | 1389778 A2 | 4/1988 |
| SU | 1457921 A1 | 2/1989 |
| SU | 1482714 A2 | 5/1989 |
| WO | WO 95/16406 | 6/1995 |
| WO | WO 95/21592 | 8/1995 |
| WO | WO 96/23455 | 8/1996 |
| WO | WO 96/24306 | 8/1996 |
| WO | WO 96/24308 | 8/1996 |

| WO | WO 96/34580 | 11/1996 |
| WO | WO 97/07752 | 3/1997 |
| WO | WO 97/15346 | 5/1997 |
| WO | WO 97/16217 | 5/1997 |
| WO | WO 97/25937 | 7/1997 |
| WO | WO 97/45073 | 12/1997 |
| WO | WO 98/19628 | 5/1998 |
| WO | WO 98/36709 | 8/1998 |
| WO | WO 98/47446 | 10/1998 |
| WO | 0 897 700 A1 | 2/1999 |
| WO | WO 99/04726 | 2/1999 |

OTHER PUBLICATIONS

Mirich, David, M.D., *Percutaneously Placed Endovascular Grafts for Aortic Aneurysms: Feasibility Study*, Radiology, vol. 170, No. 3, Part 2, pp. 1033–1037 (1989).

Parodi, J.C., M.D., et al., *Transfemoral Intraluminal Graft Implantation for Abdominal Aortic Aneuyrsms*, Annual of Vascular Surgery, vol. 5, No. 6, pp. 491–499 (1991).

Chuter, Timothy A.M., BM, BS, et al., *Transfemoral Endovascular Aortic Graft Placement*, Journal of Vascular Surgery, pp. 185–196 (Aug. 1993).

Bard XT Catina Bifurcate Stent (Brochure) (Undated).

Whitlow, Patrick L., Chapter 17: *Ostial and Bifurcation Lesions*, Textbook of Interventional Cardiology, Edited by S. Topol, pp. 317–334, (Undated).

* cited by examiner

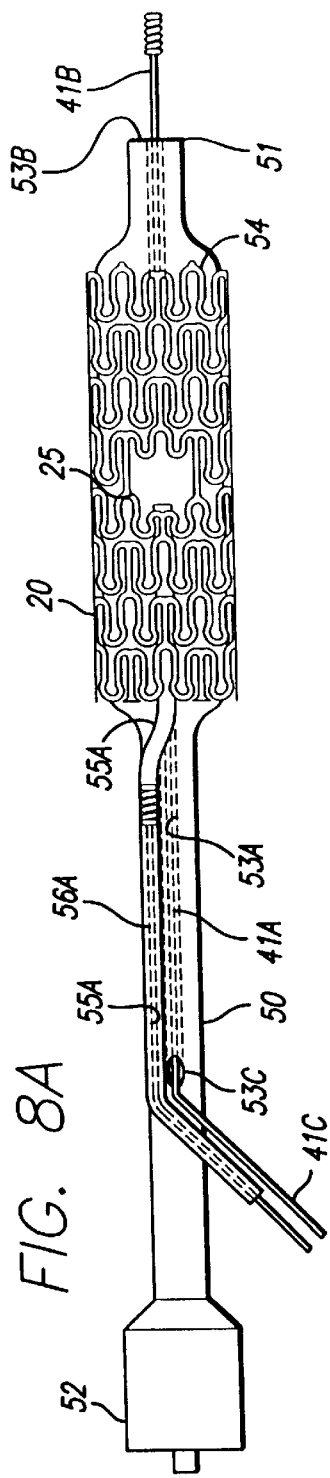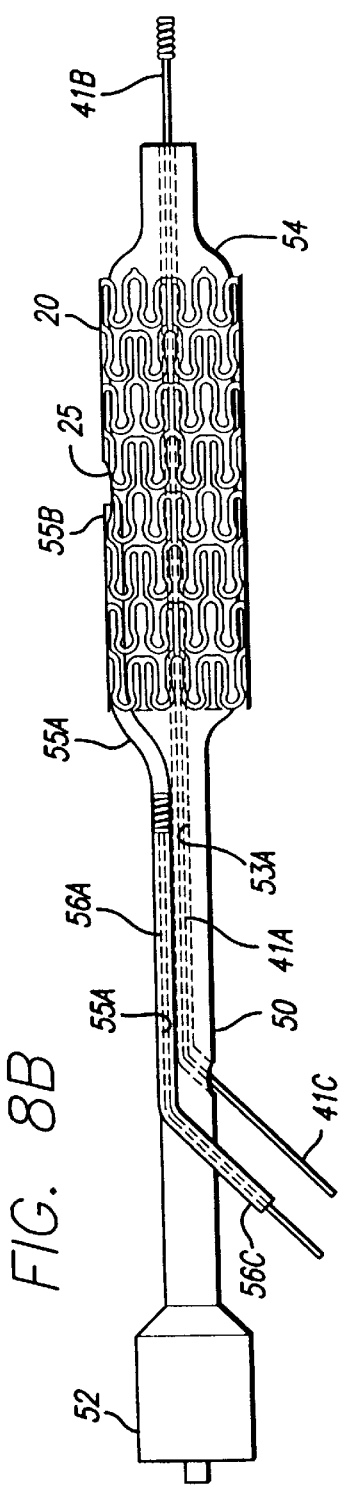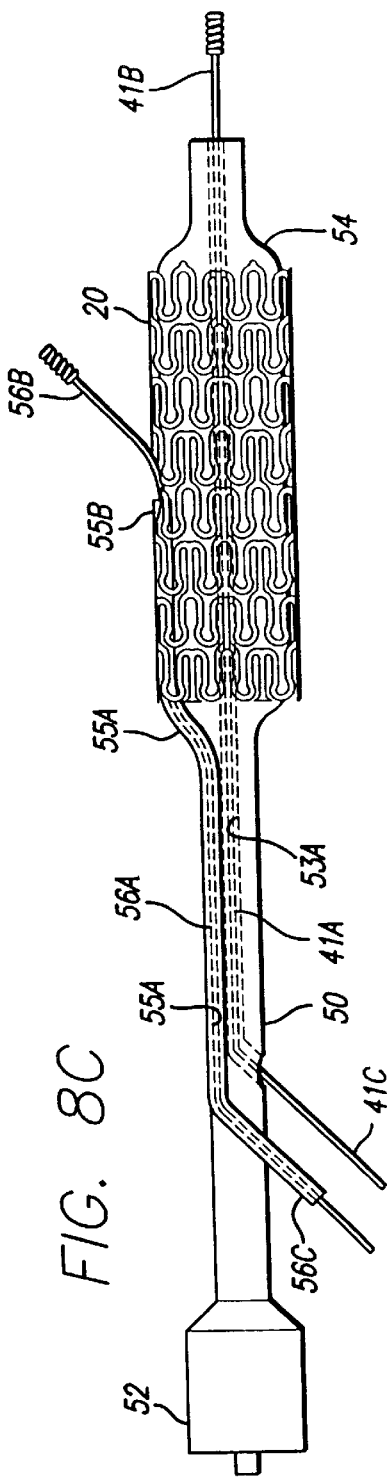

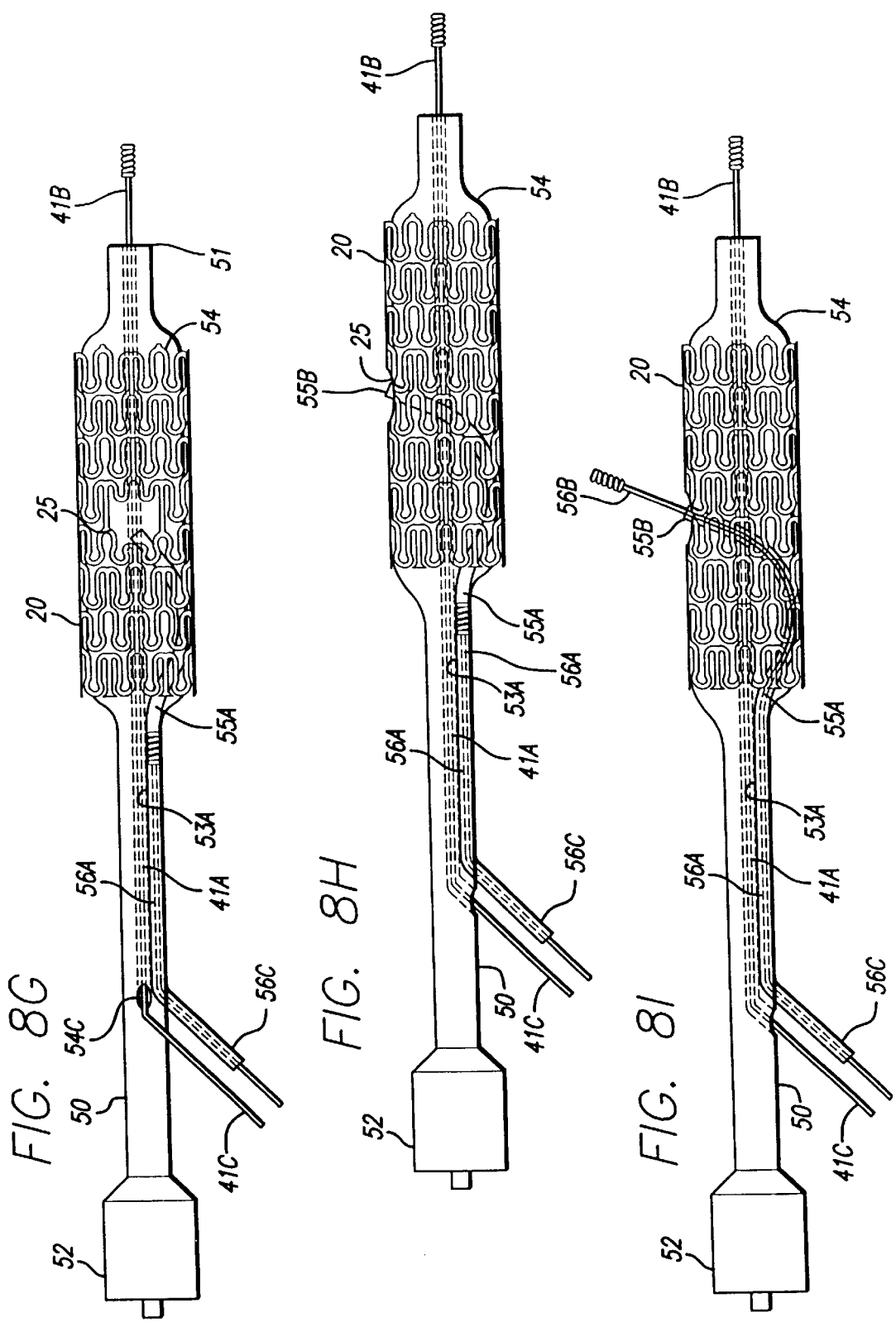

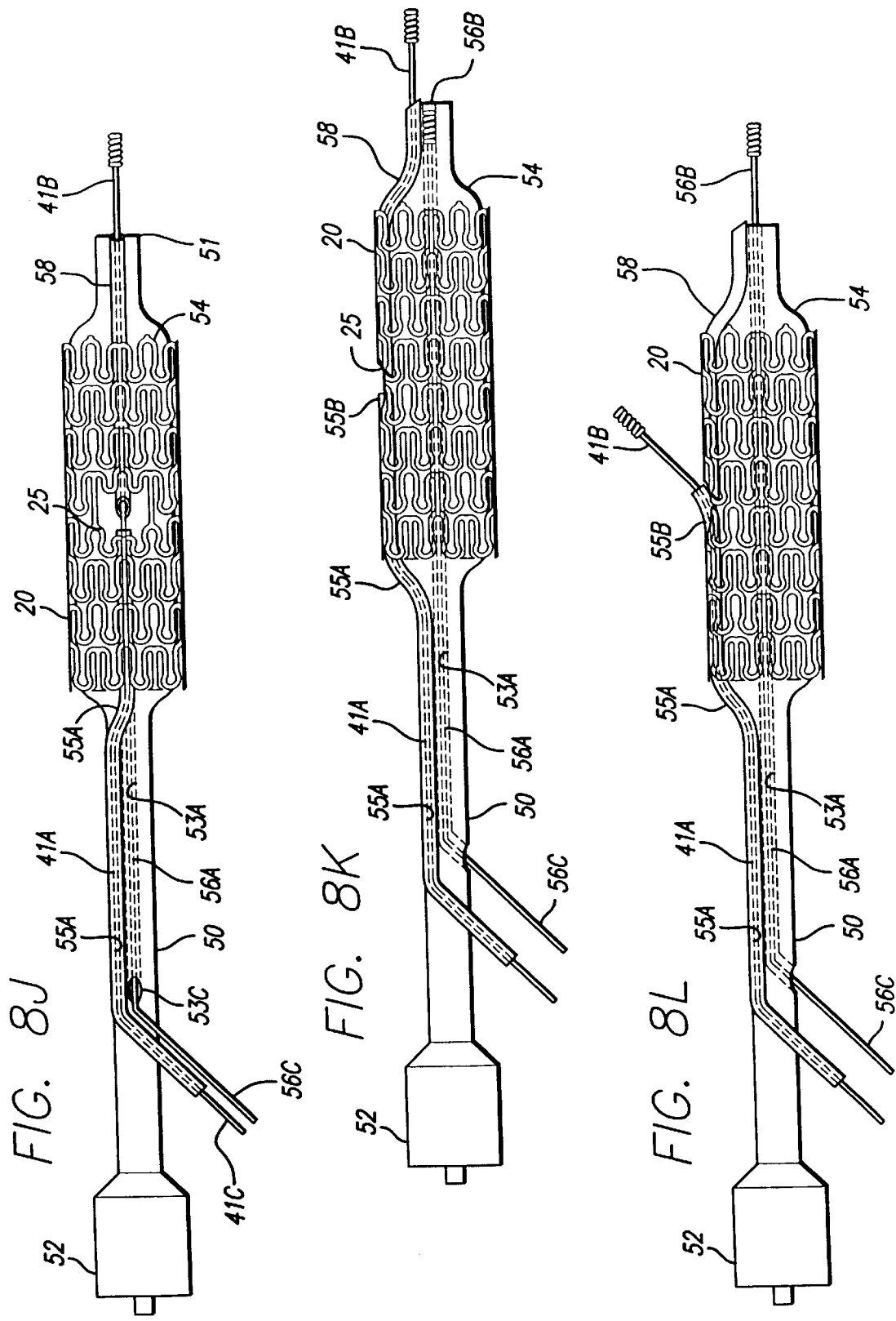

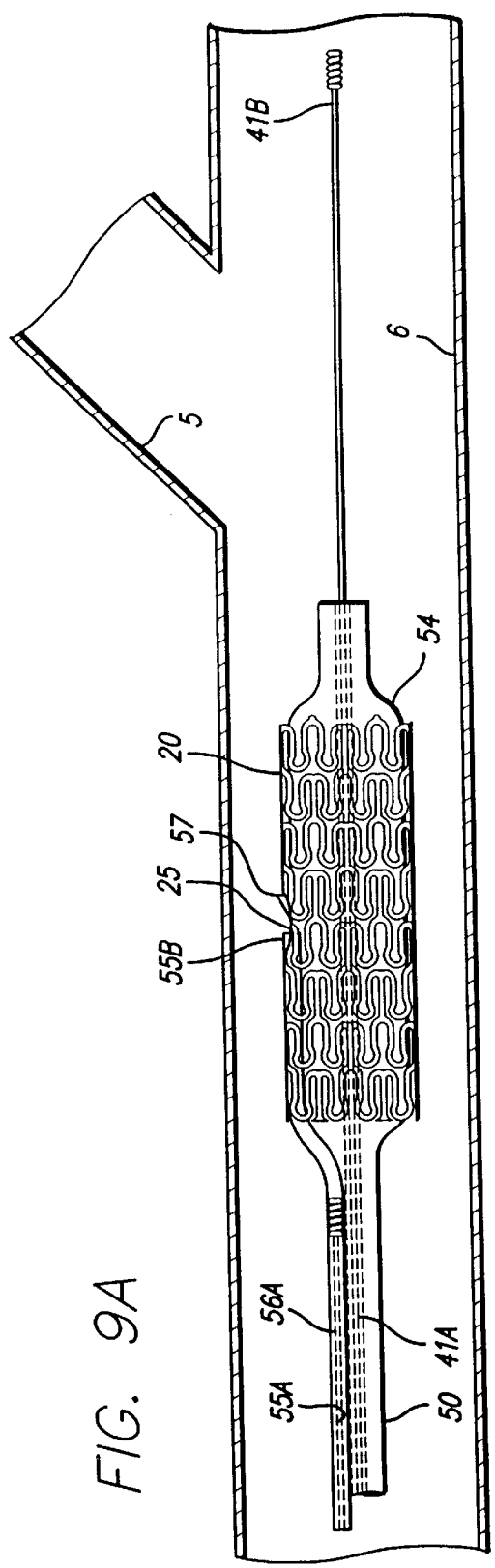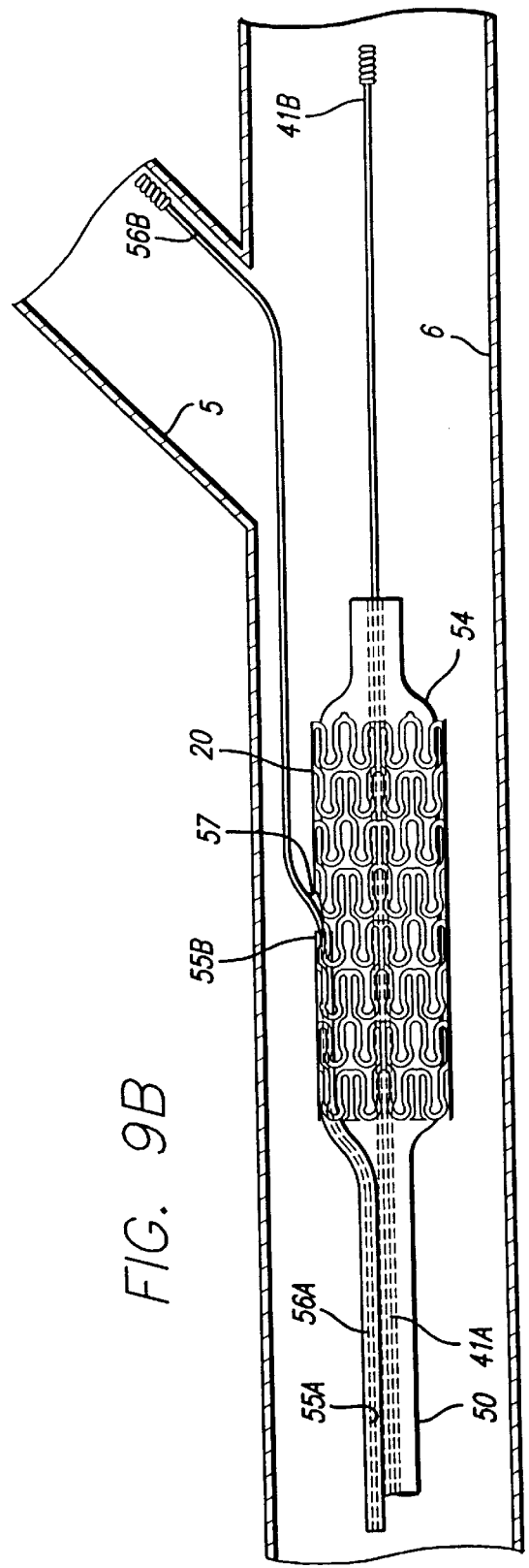

STENT AND CATHETER ASSEMBLY AND METHOD FOR TREATING BIFURCATED VESSELS

BACKGROUND OF THE INVENTION

The invention relates to stent deployment assemblies for use at a bifurcation and, more particularly, a catheter assembly for implanting one or more stents for repairing bifurcations, the aorto-ostium, and bifurcated blood vessels that are diseased, and a method and apparatus for delivery and implantation.

Stents conventionally repair blood vessels that are diseased and are generally hollow and cylindrical in shape and have terminal ends that are generally perpendicular to its longitudinal axis. In use, the conventional stent is positioned at the diseased area of a vessel and, after placement, the stent provides an unobstructed pathway for blood flow.

Repair of vessels that are diseased at a bifurcation is particularly challenging since the stent must overlay the entire diseased area at the bifurcation, yet not itself compromise blood flow. Therefore, the stent must, without compromising blood flow, overlay the entire circumference of the ostium to a diseased portion and extend to a point within and beyond the diseased portion. Where the stent does not overlay the entire circumference of the ostium to the diseased portion, the stent fails to completely repair the bifurcated vessel. Where the stent overlays the entire circumference of the ostium to the diseased portion, yet extends into the junction comprising the bifurcation, the diseased area is repaired, but blood flow may be compromised in other portions of the bifurcation. Unapposed stent elements may promote lumen compromise during neointimalization and healing, producing restenosis and requiring further procedures. Moreover, by extending into the junction comprising the bifurcation, the stent may block access to portions of the bifurcated vessel that require performance of further interventional procedures. Similar problems are encountered when vessels are diseased at their angled origin from the aorta as in the ostium of a right coronary or a vein graft. In this circumstance, a stent overlying the entire circumference of the ostium extends back into the aorta, creating problems, including those for repeat catheter access to the vessel involved in further interventional procedures.

Conventional stents are designed to repair areas of blood vessels that are removed from bifurcations and, since a conventional stent generally terminates at right angles to its longitudinal axis, the use of conventional stents in the region of a vessel bifurcation may result in blocking blood flow of a side branch or fail to repair the bifurcation to the fullest extent necessary. The conventional stent might be placed so that a portion of the stent extends into the pathway of blood flow to a side branch of the bifurcation or extend so far as to completely cover the path of blood flow in a side branch. The conventional stent might alternatively be placed proximal to, but not entirely overlaying the circumference of the ostium to the diseased portion. Such a position of the conventional stent results in a bifurcation that is not completely repaired. The only conceivable situation that the conventional stent, having right-angled terminal ends, could be placed where the entire circumference of the ostium is repaired without compromising blood flow, is where the bifurcation is formed of right angles. In such scenarios, extremely precise positioning of the conventional stent is required. This extremely precise positioning of the conventional stent may result with the right-angled terminal ends of the conventional stent overlying the entire circumference of the ostium to the diseased portion without extending into a side branch, thereby completely repairing the right-angled bifurcation.

To circumvent or overcome the problems and limitations associated with conventional stents in the context of repairing diseased bifurcated vessels, a stent that consistently overlays the entire circumference of the ostium to a diseased portion, yet does not extend into the junction comprising the bifurcation, maybe employed. Such a stent would have the advantage of completely repairing the vessel at the bifurcation without obstructing blood flow in other portions of the bifurcation. In addition, such a stent would allow access to all portions of the bifurcated vessel should further interventional treatment be necessary. In a situation involving disease in the origin of an angulated aorto-ostial vessel, such a stent would have the advantage of completely repairing the vessel origin without protruding into the aorta or complicating repeat access.

In addition to the problems encountered by using the prior art stents to treat bifurcations, the delivery platform for implanting such stents has presented numerous problems. For example, a conventional stent is implanted in the main vessel so that a portion of the stent is across the side branch, so that stenting of the side branch must occur through the main-vessel stent struts. In this method, commonly referred to in the art as the "monoclonal antibody" approach, the main-vessel stent struts must be spread apart to form an opening to the side-branch vessel and then a catheter with a stent is delivered through the opening. The cell to be spread apart must be randomly and blindly selected by recrossing the deployed stent with a wire. The drawback with this approach is there is no way to determine or guarantee that the main-vessel stent struts are properly oriented with respect to the side branch or that the appropriate cell has been selected by the wire for dilatation. The aperture created often does not provide a clear opening and creates a major distortion in the surrounding stent struts. The drawback with this approach is that there is no way to tell if the main-vessel stent struts have been properly oriented and spread apart to provide a clear opening for stenting the side-branch vessel.

Another approach to providing a main-vessel stent that does not block access to the ostium of a side-branch vessel is to cut an aperture in the side-wall of the main-vessel stent. The draw-back to this approach is that forming the aperture in this manner interferes with the structural integrity of the stent in the area of the aperture, resulting in reduced strength and scaffolding. Additionally, where such an aperture is cut into a stent having otherwise closed cells formed from stent struts, the perimeter of the aperture will have open cells and unjoined stent struts presenting a jagged perimeter that may interfere with crossing of the aperture by a guide wire or catheter if subsequent treatment of the side-vessel is required.

In another prior art method for treating bifurcated vessels, commonly referred to as the "Culotte technique," the side-branch vessel is first stented so that the stent protrudes into the main vessel. A dilatation is then performed in the main vessel to open and stretch the stent struts extending across the lumen from the side-branch vessel. Thereafter, the main-vessel stent is implanted so that its proximal end overlaps with the side-branch vessel. One of the drawbacks of this approach is that the orientation of the stent elements protruding from the side-branch vessel into the main vessel is completely random. Furthermore the deployed stent must be recrossed with a wire blindly and arbitrarily selecting a particular stent cell. When dilating the main vessel stretching the stent struts is therefore random, leaving the possibility of restricted access, incomplete lumen dilatation, and major stent distortion.

In another prior art device and method of implanting stents, a "T" stent procedure includes implanting a stent in the side-branch ostium of the bifurcation followed by stenting the main vessel across the side-branch ostium. In another prior art procedure, known as "kissing" stents, a stent is implanted in the main vessel with a side-branch stent partially extending into the main vessel creating a double-barreled lumen of the two stents in the main vessel distal to the bifurcation. Another prior art approach includes a so-called "trouser legs and seat" approach, which includes implanting three stents, one stent in the side-branch vessel, a second stent in a distal portion of the main vessel, and a third stent, or a proximal stent, in the main vessel just proximal to the bifurcation.

All of the foregoing stent deployment assemblies suffer from the same problems and limitations. Typically, there is uncovered intimal surface segments on the main vessel and side-branch vessels between the stented segments. An uncovered flap or fold in the intima or plaque will invite a "snowplow" effect, representing a substantial risk for subacute thrombosis, and the increased risk of the development of restenosis. Further, where portions of the stent are left unapposed within the lumen, the risk for subacute thrombosis or the development of restenosis again is increased. The prior art stents and delivery assemblies for treating bifurcations are difficult to use, making successful placement nearly impossible. Further, even where placement has been successful, the side-branch vessel can be "jailed" or covered so that there is impaired access to the stented area for subsequent intervention. The present invention solves these and other problems as will be shown.

In addition to problems encountered in treating disease involving bifurcations for vessel origins, difficulty is also encountered in treating disease confined to a vessel segment but extending very close to a distal branch point or bifurcation which is not diseased and does not require treatment. In such circumstances, very precise placement of a stent covering the distal segment, but not extending into the ostium of the distal side-branch, may be difficult or impossible. The present invention also offers a solution to this problem.

References to distal and proximal herein shall mean: the proximal direction is moving away from or out of the patient and distal is moving toward or into the patient. These definitions will apply with reference to body lumens and apparatus, such as catheters, guide wires, and stents.

SUMMARY OF THE INVENTION

The invention provides for improved stent designs and stent delivery assemblies for repairing a main vessel and side-branch vessel forming a bifurcation, without compromising blood flow in other portions of the bifurcation, thereby allowing access to all portions of the bifurcated vessels should further interventional treatment be necessary. The stent delivery assemblies of the invention all share the novel feature of containing, in addition to a tracking guide wire, a second positioning wire which affects rotation and precise positioning of the assembly for deployment of the stent.

A stent is provided for implanting in the main vessel adjacent to a bifurcation in which a cylindrical member has distal and proximal ends and an outer wall surface therebetween, which can typically be similar to the outer wall surface of stents used in the coronary arteries. An aperture is formed in the outer wall surface of the apertured stent and is sized and positioned on the outer wall surface so that when the apertured stent is implanted in the main vessel, the aperture is aligned with the side-branch vessel providing unrestricted blood flow from the main vessel through to the side-branch vessel. Deployment of the apertured stent is accomplished by a novel stent delivery system adapted specifically for treating bifurcated vessels.

The aperture is formed in the outer wall of the stent by configuring the undulating or serpentine pattern of the cylindrical elements of the stent to provide the aperture. Reconfiguring the pattern in this manner provides an aperture perimeter formed of closed stent cells. This construction provides increased strength in the area of the aperture as well as improved scaffolding of the vessel wall surrounding the ostium.

In general, the aperture is formed in the stent by adjusting the pattern of stent cells and stent struts so that the size of the stent cell in the region of the stent surrounding the aperture is less than the stent cells in the remainder of the stent. Preferably, the stent cells in the region including the aperture are half the size of remaining stent cells. The smaller cell size in the region of the aperture results in an aperture perimeter that is smaller and denser, providing both increased scaffolding of the vessel wall surrounding the ostium of a side-branch vessel as well as providing a smoother lumen for accessing the side-branch vessel should subsequent treatment of the side-branch vessel be necessary.

The stent delivery system of the present invention further includes a main-vessel catheter for delivering a stent in the main vessel after the side-branch vessel has been stented. The main-vessel catheter includes a tracking guide wire lumen extending through at least a portion thereof, and adapted for receiving a tracking guide wire for slidable movement therein. An expandable member is positioned near the main-vessel catheter distal end for delivering and implanting a main-vessel (apertured) stent in the main vessel. The main-vessel stent includes an aperture on its outer surface which aligns with the side-branch vessel. A positioning guide wire lumen is associated with the expandable member, and is sized for slidably receiving the stent-positioning guide wire. The stent-positioning guide wire slides within the positioning guide wire lumen to orient the expandable member so that it is positioned adjacent to, but not in, the side-branch vessel with the stent aperture facing the side-branch ostium.

In one embodiment, the main-vessel catheter assembly includes the so-called rapid exchange catheter features which are easily exchangeable for other catheters while the tracking and positioning guide wires remain positioned in the side-branch vessel and the main vessel, respectively. In an alternate embodiment, both catheters may be of the "over-the-wire" type.

The present invention further includes a method for delivering the main-vessel (apertured) stent in the bifurcated vessel.

In the event that the main vessel is to be stented (with the stent placed across the bifurcation site), the proximal end of the main-vessel guide wire is inserted into the distal end of the guide wire lumen of the main-vessel catheter. The main-vessel catheter would then be advanced into the body until the catheter is within one cm or so of the target site. The distal end of the second (integrated, stent-positioning) guide wire, which resides in the main-vessel catheter during delivery to the main vessel, is then advanced by having the physician push the positioning wire from outside the body. The distal end of the stent-positioning wire travels through the positioning guide wire lumen and passes underneath the proximal half of the stent until it exits at the site of the stent aperture. The catheter is then advanced distally until resistance is felt from the stent-positioning guide wire pushing up against the ostium of the side-branch vessel indicating that the stent aperture is correctly facing the side-branch vessel ostium. If a stent has already been implanted in the side-branch vessel, this resistance also ensures that the aperture of the main vessel stent is aligned with the proximal end of the side-branch stent. Thereafter, the expandable member on the main-vessel catheter is inflated, thereby expanding and implanting the main-vessel stent into contact with the main vessel, with the aperture in the stent providing a flow path for the blood from the main vessel through to the side-branch vessel without any obstructions. The expandable member is deflated and the main-vessel catheter is removed from the body. The main-vessel catheter is designed so that both the main-vessel guide wire and side-branch wire can be left in their respective vessels should sequential or simultaneous high pressure balloon inflation be required in each of the vessels in order to complete the stenting procedure. The presence of the stent-positioning wire in the stent aperture permits catheter access through this aperture into the side-branch vessel for balloon inflation to smooth out the aperture in the main-vessel stent. This additional step is a matter of physician choice.

Utilizing this method, the main vessel can be stented without the need for stenting the side-branch vessel. An advantage of this embodiment is that a major side branch, not diseased and requiring treatment, exiting from a main vessel requiring stenting, may be protected by the positioning wire while the main vessel is stented. If "snowplowing" compromise or closure of the side-branch vessel occurs with main-vessel stenting, then access is already present and guaranteed for stenting of the side-branch vessel over the wire already in place in the manner described above. This will allow confident stenting of a main vessel segment containing a major side branch. In this usage, only if compromise or occlusion of the side branch occurs, will additional stenting of the side branch be required.

In an alternative embodiment, the stent to be implanted in the main-vessel is mounted on a main-vessel catheter having an expandable section including two expandable balloons closely spaced together but separated sufficiently so that an exit port formed in the wall of the main-vessel catheter is exposed, allowing a stent-positioning guidewire to exit the catheter. In normal use, the stent is mounted such that the aperture of the stent is aligned with the exit port, allowing the stent-positioning guidewire to extend out of the exit port and through the stent. In this embodiment, the main-vessel catheter is advanced into the body until the catheter is within one cm or so of the target site. The distal end of the stent-positioning guide wire, which resides in the main-vessel catheter during delivery to the main vessel, is then advanced by having the physician push the positioning wire from outside the body. The distal end of the stent-positioning wire travels through the positioning guide wire lumen until it exits through the exit port between the balloons at the site of the stent aperture. The catheter is then advanced distally until resistance is felt from the stent-positioning guide wire pushing up against the ostium of the side-branch vessel indicating that the stent aperture is correctly facing the side-branch vessel ostium. The remainder of the method is as described above. The main-vessel catheter is designed so that both the main-vessel guide wire and side-branch wire can be left in their respective vessels should sequential or simultaneous high pressure balloon inflation be required in each of the vessels in order to complete the stenting procedure. A further advantage of this method is that both the main-vessel guide wire and side-branch wires are contained within the catheter body, allowing for use of either an integrated main-vessel/side-branch guide wire system or simply running two separate guide-wires through a central lumen of the catheter. Alternatively, the main-vessel catheter may include two separate lumens to accommodate the main-vessel and side-branch guide wires.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIGS. 8A–8C depict an elevational view, partially in section, of a main-vessel catheter assembly in which the main vessel stent has an aperture on its outer surface.

FIGS. 8G–8I depict a n elevational view, partially in section, of an alternative embodiment of the main-vessel catheter of FIGS. 8A–8C in which the guide wire lumen is angled to pass under the stent and exit through the stent aperture.

FIGS. 8J–8L depict an elevational view, partially in section, of an alternative embodiment of the main-vessel catheter of FIGS. 8A–8C in which a portion of the guide wire lumen passes under the stent.

FIGS. 9A–9D are elevational views, partially in section, depicting the main-vessel catheter assembly of FIG. 8A and the main-vessel stent in which two guide wires are used to correctly position the main vessel stent so that the aperture in the stent is aligned with the side-branch vessel.

DETAILED DESCRIPTION OF THE PREFERRED EMBODIMENTS

Figure 1:
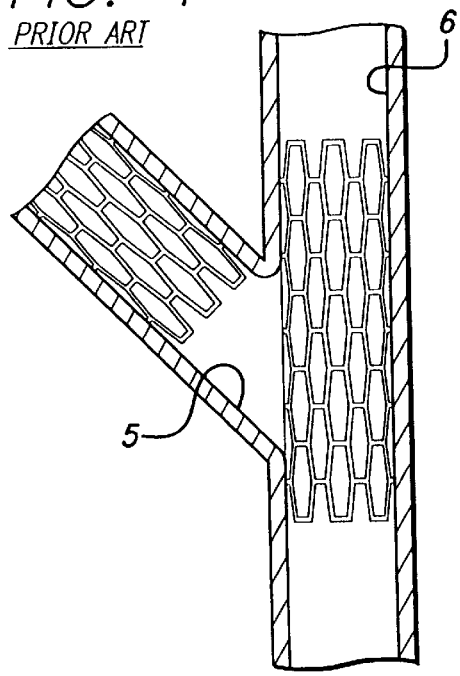
FIG. 1 is an elevational view of a bifurcation in which a prior art "T" stent is in a side-branch ostium followed by the stenting of the main vessel across the branch ostium.

The present invention includes an assembly and method for treating bifurcations in, for example, the coronary arteries, veins, arteries, and other vessels in the body. Prior art attempts at implanting intravascular stents in a bifurcation have proved less than satisfactory. For example, FIGS. 1–4 depict prior art devices which include multiple stents being implanted in both the main vessel and a side-branch vessel. In FIG. 1, a prior art "T" stent is implanted such that a first stent is implanted in the side branch 5 near the ostium of the bifurcation, and a second stent is implanted in the main vessel 6, across the side-branch ostium. With this approach, portions of the side-branch vessel are left uncovered, and blood flow to the side-branch vessel must necessarily pass through the main-vessel stent, causing possible obstructions or thrombosis.

Figure 2:
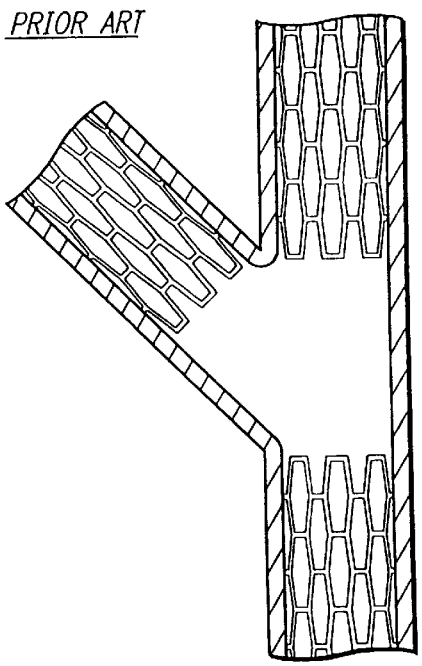
FIG. 2 is an elevational view of a bifurcation in which "touching" prior art stents are depicted in which one stent is implanted in the side branch, a second stent implanted in a proximal portion of the main vessel next to the branch stent, with interrupted placement of a third stent implanted more distally in the main vessel.
Figure 3:
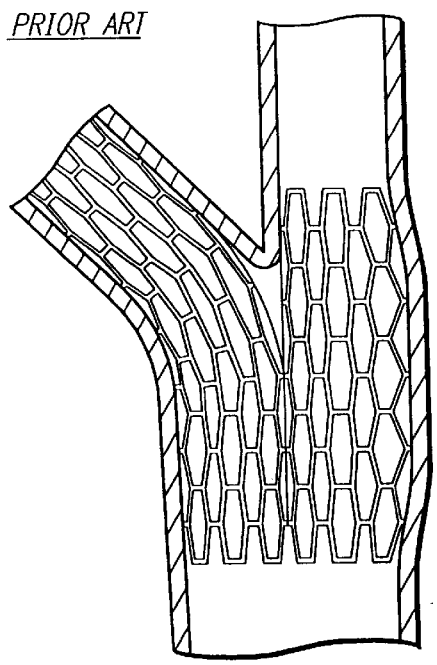
FIG. 3 is an elevational view of a bifurcation depicting "kissing" stents where a portion of one stent is implanted in both the side-branch and the main vessel and adjacent to a second stent implanted in the main vessel creating a double-barreled lumen in the main vessel distal to the bifurcation.
Figure 4:
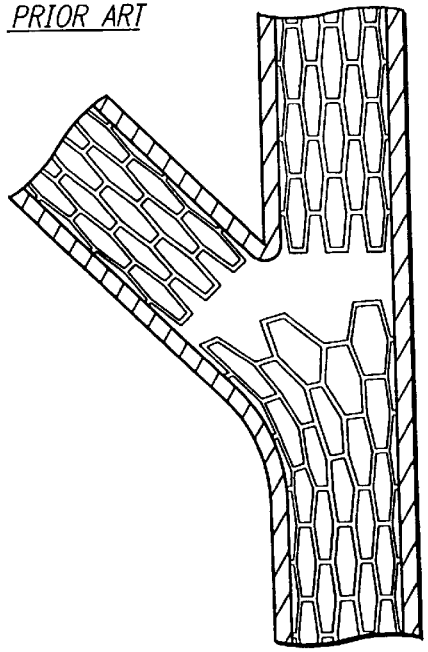
FIG. 4 is an elevational view of a prior art "trouser legs and seat" stenting approach depicting one stent implanted in the side-branch vessel, a second stent implanted in a proximal portion of the main vessel, and a close deployment of a third stent distal to the bifurcation leaving a small gap between the three stents of an uncovered luminal area.

Referring to FIG. 2, three prior art stents are required to stent the bifurcation. In FIG. 3, the prior art method includes implanting two stents side by side, such that one stent extends into the side-branch vessel and the main vessel, and the second stent is implanted in the main vessel. This results in a double-barreled lumen which can present problems such as thrombosis, and turbulence in blood flow. Referring to the FIG. 4 prior art device, a first stent is implanted in the side-branch vessel, a second stent is implanted in a proximal portion of the main vessel, and a third stent is implanted distal to the bifurcation, thereby leaving a small gap between the stents and an uncovered luminal area.

Figure 7A:
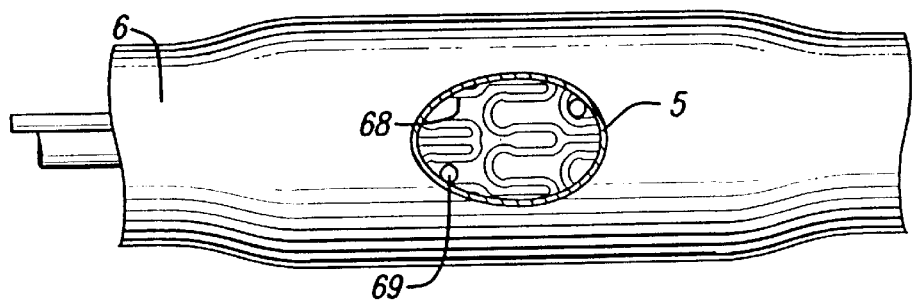
FIGS. 7A and 7B are cross-sectional views looking down the side-branch vessel at an expanded main vessel prior art stent in which a random, sub-optimal stent cell was entered and expanded.
Figure 7B:
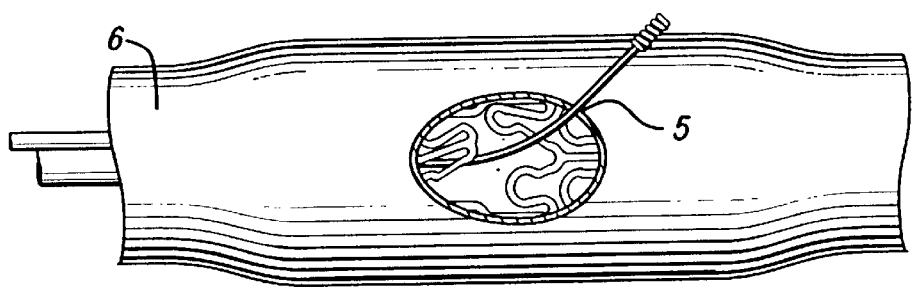
Figure 7C:
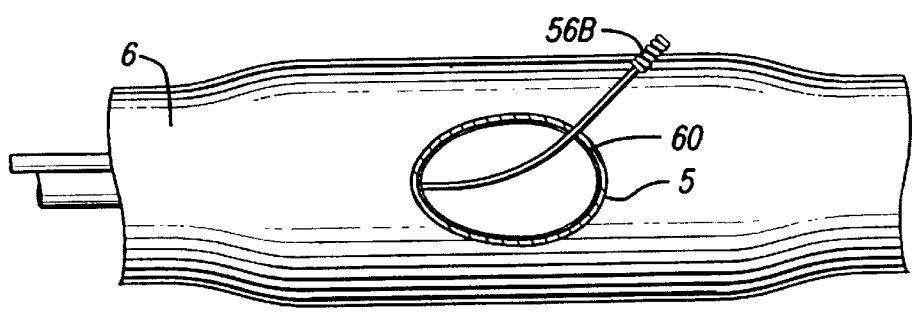
FIG. 7C is a cross-sectional view looking down the side-branch vessel at an expanded main-vessel stent of the present invention showing the alignment between the aperture of the stent and the ostium of the side-branch vessel, allowing for free flow of blood between the vessels.

Prior art devices that have attempted to first stent the main vessel and randomly select a stent cell to expand for alignment with the side-branch vessel, have generally failed. One such approach, known as the "monoclonal antibody" approach, as depicted in FIGS. 7A and 7B, depict what can happen when an inappropriate target stent cell is selected randomly and then expanded by a high pressure balloon. As shown in FIG. 7A, which is a view looking down side-branch vessel 5 in partial cross-section at a prior art stent 68, the physician randomly selects stent cell 69 which is a sub-optimal cell to expand with the balloon portion of a catheter. As depicted in FIG. 7B, after balloon expansion in the suboptimal cell 69, entry into the cell with a catheter may be impossible or, if accomplished, expansion of the balloon may be incomplete. The aperture created will be inadequate and major distortion in the adjacent stent struts may occur. Consequences may include subacute thrombosis or restenosis. With the present invention, as shown in FIG. 7C, the aperture of the stent is oriented optimally with respect to the side-branch ostium prior to deployment of the stent using a method of the present invention to be described below. The aperture of the present invention as shown in FIG. 7C, guarantees an optimal aperture essentially devoid of stent struts blocking the blood flow path from the main vessel to the side-branch vessel.

All of the prior art devices depicted in FIGS. 1–4 and 7A–7B have various drawbacks which have been solved by the present invention. The stent of the present invention can be implanted in the main vessel where access to a side-branch vessel is necessary to treat a number of angulated ostial lesions including, but not limited to, the following:

1. The ostium of a left anterior descending artery (LAD) where there is a circumflex or trifurcation vessel at less than 90° in its departure from the LAD.
2. The ostium of the circumflex artery or a trifurcation in a similar situation as number 1.
3. The ostium of a sizeable diagonal.
4. The LAD just distal to, but sparing, the origin of a diagonal.
5. The ostium of a circumflex marginal artery with an angulated take-off.
6. Disease in the circumflex artery just distal to a marginal take-off, but sparing that take-off.
7. The aorta-ostium of a right coronary artery with an angled take-off.
8. The origin of an angulated posterior descending artery.
9. The origin of an LV extension branch just at and beyond the crux, sparing the posterior descending artery.
10. The ostium of an angulated vein graft origin.
11. Any of many of the above locations in conjunction with involvement of the bifurcation and an alternate vessel.

The main vessel stent of the present invention may be used as a solo device, or it can be used in conjunction with an angled stent to treat the foregoing indications.

Figure 5A:
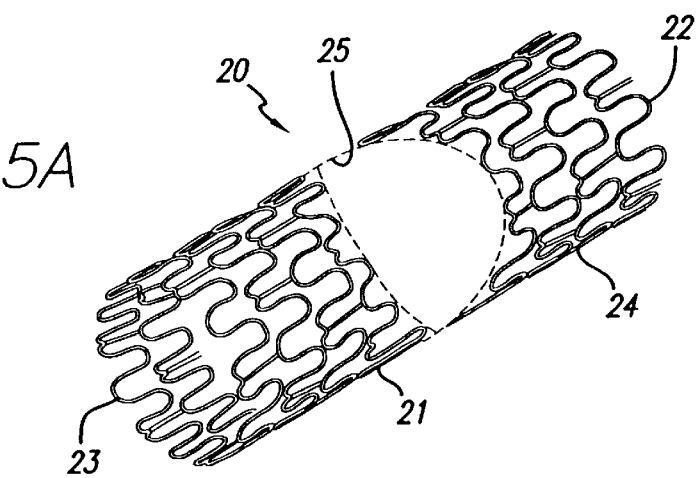
FIG. 5A is a perspective view depicting the main-vessel stent of the present invention in which an aperture is formed on the outer surface of at least a portion of the stent.
Figure 5B:
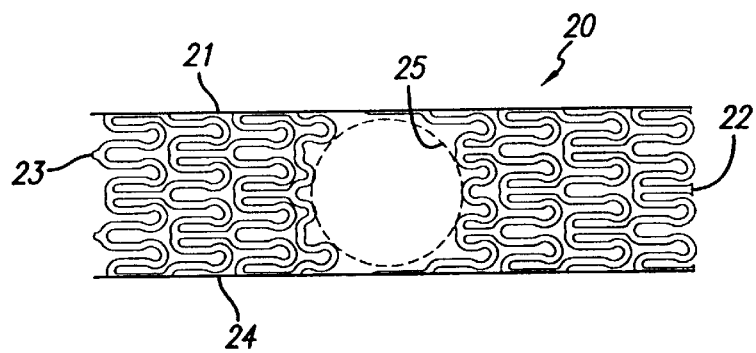
FIG. 5B is a side elevational view of the main-vessel stent of FIG. 5A.

In keeping with the invention, as depicted in FIGS. 5A and 5B; main-vessel stent 20 is configured for deployment in main-vessel 6. Main-vessel stent 20 includes cylindrical member 21 having distal end 22 and proximal end 23. Main-vessel stent 20 includes outer wall surface 24 which extends between distal end 22 and proximal end 23 and incorporates aperture 25 on outer wall surface 24. Aperture 25 is configured so that, upon expansion, it approximates the diameter of the ostium of side-branch vessel 5. Where main-vessel stent 20 is used in conjunction with a stent implanted in side-branch vessel 5, the aperture 25 of main-vessel stent 20 is sized so that, upon expansion, the aperture approximates the diameter of the expanded side-branch stent. When main-vessel stent 20 is implanted and expanded into contact with main-vessel 6, aperture 25 is aligned with side-branch vessel 5 and proximal end 14 of proximal angled stent, thereby providing an unrestricted blood flow path from the side-branch vessel to the main vessel. Unlike the prior art, the main-vessel catheter allows selection and positioning of an aperture at the side-branch ostium. Furthermore, it provides for the positioning of a guide wire during main-vessel stent deployment which can be used for additional intervention if necessary. In the prior art techniques access to a side-branch is through a randomly selected stent element ("cell") and is only possible after deployment of the stent. The precise positioning of aperture 25 is optional and aperture 25 could be positioned either closer to the proximal or distal end of stent 20.

Main-vessel stent 20 can be formed from any of a number of materials including, but not limited to, stainless steel alloys, nickel-titanium alloys (the NiTi can be either shape memory or pseudoelastic), tantalum, tungsten, or any number of polymer materials. Such materials of manufacture are known in the art. Further, main-vessel stent 20 can have virtually any pattern including those known to prior art stents. In one configuration, main-vessel stent 20 is formed from a stainless steel material and has a plurality of cylindrical elements connected by connecting members, wherein the cylindrical elements have an undulating or serpentine pattern. Such a stent is disclosed in U.S. Pat. No. 5,514,154 and is manufactured and sold by Advanced Cardiovascular Systems, Inc., Santa Clara, Calif. The stent is sold under the tradename MultiLink® Stent. Such stents can be modified to include the novel features of main-vessel stent 20 (the aperture).

As is depicted in FIGS. 5A and 5B, the aperture 25 is formed in main-vessel stent 25 by specifically configuring the undulating or serpentine pattern of the cylindrical elements of the stent to provide the aperture. Reconfiguring the pattern in this manner provides for increased strength at the border of the aperture as well as improved scaffolding of the vessel wall compared to a stent in which an opening is simply cut into the stent wall leaving open stent cells or unconnected stent struts, or where a random stent cell has been expanded to provide the aperture. One advantage to forming aperture 25 in the manner of the present invention is that aperture 25 has a perimeter formed of closed stent cells. This structure provides for improved stent strength in the border of the stent surrounding the aperture, and also provides improved scaffolding of the main-vessel wall 6 surrounding the ostium of side-branch vessel 6. The closed stent cells surrounding aperture 25 also provide a smoother, more regular aperture boundary that is less likely to interfere with subsequent crossing of aperture 25 by a guide wire or catheter should subsequent treatment of side-branch vessel 5 be required.

Figure 6:
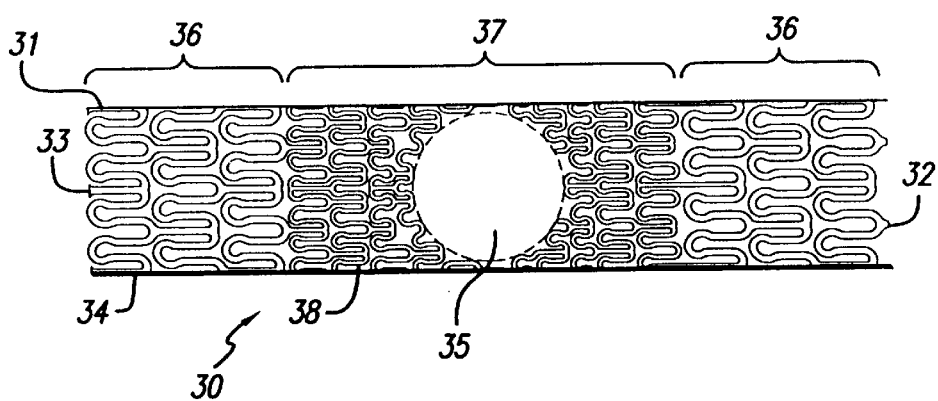
FIG. 6 is a side elevational view of another embodiment of the main-vessel stent of the present invention.

In an another embodiment depicted in FIG. 6, main-vessel stent 30 includes cylindrical member 31 having distal end 32 and proximal end 33. Main-vessel stent 30 includes outer wall surface 34 which extends between distal end 32 and proximal end 33. In this embodiment, main-vessel stent 30 includes stent sections 36 which include cylindrical elements having cells of like size. Located between stent sections 36 is central stent section 37, in which is formed an aperture 35. The cells 38 making up the cylindrical elements comprising central stent section 37 have a reduced size compared to the cells of stent sections 36; for example, each cell in central stent section 37 may be only half the size of a cell of stent sections 36. Reducing the cell size in central stent section 37 provides for a smoother, more uniform boundary of aperture 35, which may be advantageous, especially in those instances where a stent must be implanted in a side-branch vessel after implantation of main-vessel stent 30 in the main-vessel.

For convenience, all references to the main-vessel stent of the present invention will hereinafter refer to main-vessel stent 20. It will be understood, however, that the methods describing the delivery of the main-vessel stents of present invention are equally applicable to each embodiment of the main-vessel stent disclosed herein.

Main-vessel stent 20 preferably is a balloon-expandable stent that is mounted on a balloon portion of a catheter and crimped tightly onto the balloon to provide a low profile delivery diameter. After the catheter is positioned so that the stent and the balloon portion of the catheter are positioned either in the side-branch or the main vessel, the balloon is expanded, thereby expanding the stent beyond its elastic limit into contact with the vessel. Thereafter, the balloon is deflated and the balloon and catheter are withdrawn from the vessel, leaving the stent implanted. Deployment of the main-vessel stent is accomplished by a novel stent delivery system adapted specifically for treating bifurcated vessels. The main-vessel stent could be made to be either balloon expandable or self-expanding.

If necessary, main-vessel 6 also can be stented after stenting the side-branch vessel 5. In that regard, and in keeping with the invention, main-vessel catheter assembly 50 is provided for implanting main-vessel stent 20, as depicted in FIGS. 8A to 9E. In one embodiment, as shown in FIGS. 8A–8C, main-vessel catheter 50 includes distal end 51 which is configured for advancement within the patient's vasculature, and proximal end 52 which remains outside the patient. The main-vessel catheter includes guide wire lumen 53A having distal end 53B and side port 53C, which is proximal to the balloon portion of the catheter. Side port 53C is provided in a so-called rapid-exchange catheter system which includes a slit (not shown) as is known in the art. Expandable member 54 is located near distal end 51 of main-vessel catheter 50. Typically, expandable member 54 is a non-distensible balloon of the type known in the art for delivering and expanding stents.

In further keeping with the invention, positioning guide wire lumen 55A is positioned partly on the catheter shaft and partly on expandable member 54, and is configured for slidably receiving integrated stent-positioning guide wire 56A. Prior to stent delivery, guide wire 56A resides in guide wire lumen 55A and only during stent delivery is it then advanced into and through angled portion 55B of the lumen.

Figure 8D:
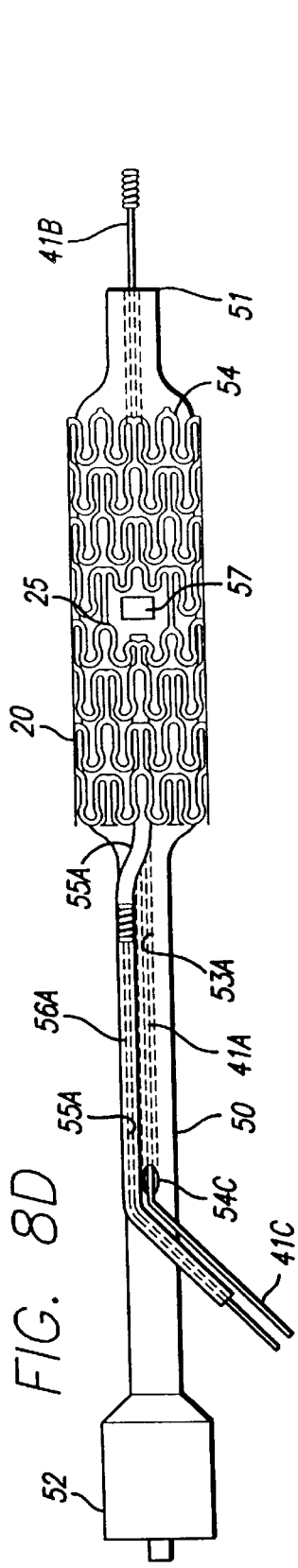
FIGS. 8D–8F depict an elevational view, partially in section, of the main-vessel catheter of FIGS. 8A–8C with a ramp to help orient and advance the guide wire through the aperture in the main-vessel stent.
Figure 8E:
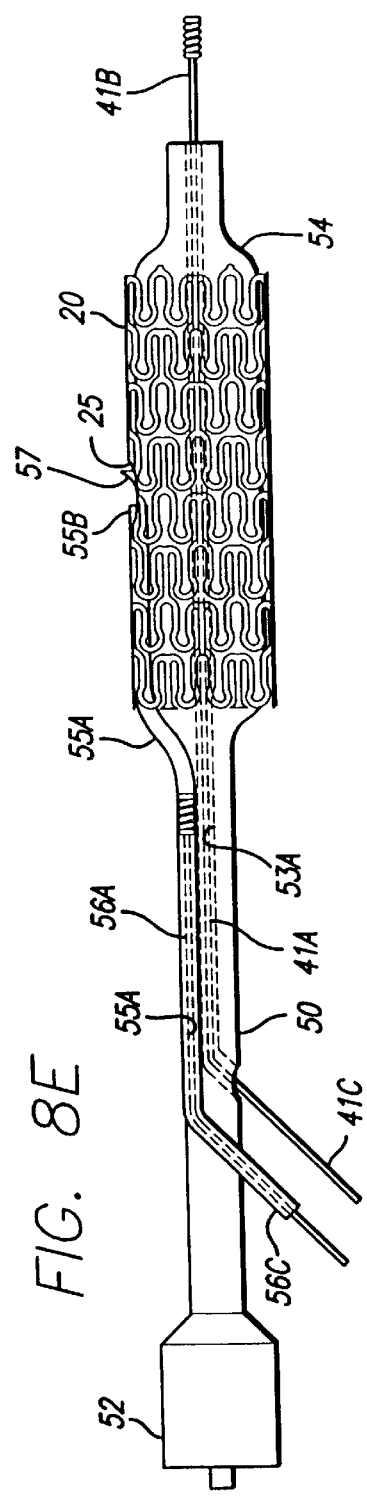
Figure 8F:
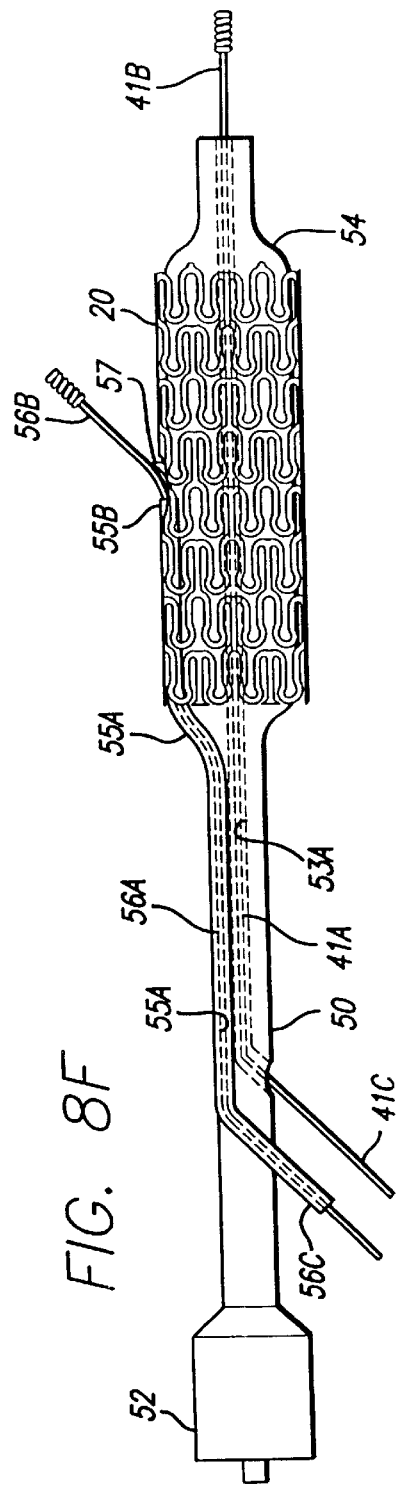
Figure 9C:
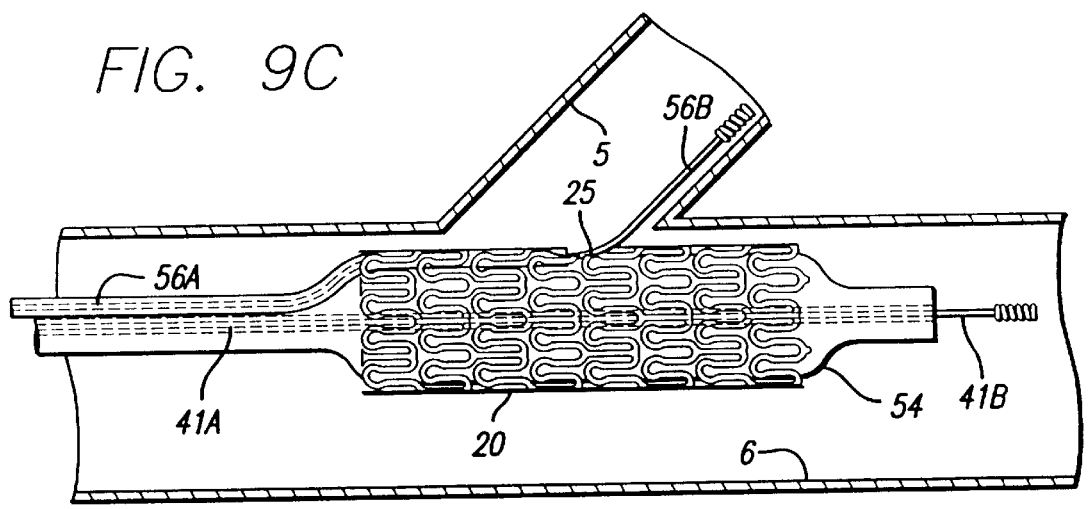
Figure 9D:
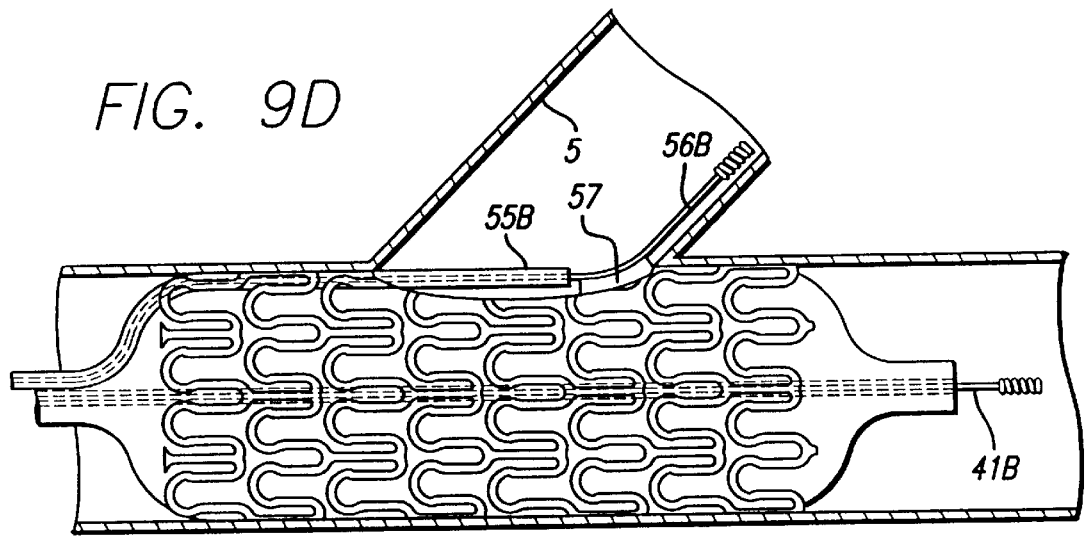

Other embodiments for implanting main-vessel stent 20 in main-vessel 6 are depicted, for example, in FIGS. 8D–8F. This embodiment is identical to that depicted in FIGS. 8A–8C, with the addition of ramp 57 which is mounted on balloon 35 and provides a slight incline for guide wire 56A as it exits guide wire lumen 55A. As the guide wire slides along ramp 57, distal portion 56B of the guide wire will move radially outwardly which helps position the guide wire and orient it into the side-branch vessel. In another embodiment for implanting the main-vessel stent in the main vessel, as depicted in FIGS. 8G–8I, guide wire lumen 55A passes underneath main-vessel stent 20 and on top of balloon 35. The distal end 55B curves along the balloon so that as guide wire 56B advances out of the distal end 55B of the lumen, it is traveling radially outwardly so that it can more easily locate and advance into the side-branch vessel 5.

In still another embodiment for implanting main-vessel stent 20 in the main-vessel 6, as depicted in FIGS. 8J–8L, guide wire lumen 55A is positioned under stent 20 and terminates at distal end 55B in the middle of aperture 25. The distal end 55A of the guide wire lumen will spring outwardly which facilitates advancing guide wire distal end 41B into the side branch vessel. A distal guide wire lumen 58 is attached to the balloon 35 outer surface and extends from aperture 25 to essentially the distal end of the catheter.

In one method of implanting main-vessel stent 20 in main-vessel 6, as depicted in FIGS. 8A–8I and 9A–9D, guide wire 41A remains in position in main-vessel 6, while the side-branch guide wire 36A is withdrawn from the patient. Main-vessel catheter 50 is backloaded onto guide wire 41A by inserting proximal end 41B of the wire into the distal end of the catheter and into guide wire lumen 53A. Main-vessel catheter 50 is advanced over guide wire 41A and viewed under fluoroscopy until main-vessel stent 20 is positioned in main-vessel 6, just proximal to side-branch vessel 5. The distal end 56B of the integrated stent-positioning guide wire 56A is then advanced by the physician pushing on proximal end 56C from outside the body.

The distal end 56B of wire 56A advances into and through positioning guide wire lumen 55A and passes underneath the proximal end of the main-vessel stent 20 and exits the angled portion 55B of the lumen and enters side-branch vessel 5. The main-vessel catheter 50 is then advanced distally into the main vessel until resistance is felt from the stent-positioning guide wire 56A pushing up against the ostium of the side-branch vessel. The stiffness of stent-positioning guide wire 56A causes the main-vessel catheter 50, with main-vessel stent 20 thereon, to rotate so that aperture 25 is facing the side-branch vessel 5 ostium and proximal angled stent 10 already implanted.

Expandable member 54, which is typically a non-distensible expandable balloon, is inflated thereby expanding main-vessel stent 20 into contact with main-vessel 6. Aperture 25 correspondingly expands and when properly aligned, provides a blood flow path between aperture 25 and proximal angled stent 10 implanted in side-branch vessel 5. As can be seen in FIGS. 8A–8I and 9A–9D, positioning guide wire lumen 55A is positioned on expandable member 54, such that when the expandable member is inflated, positioning guide wire lumen 55A does not interfere with implanting main-vessel stent 20. After the main-vessel stent is implanted in the main vessel, expandable member 54 is deflated, and main-vessel catheter 50 withdrawn from the patient.

In an alternative method of implanting main-vessel stent 20 in main-vessel 6 as depicted in FIGS. 8J–8L, tracking guide wire 41A is advanced through guide wire lumen 55A and guide wire lumen 58 so that it advances distally of the distal end 51 of the catheter. Thus, guide wire distal end 41B is advanced into the main vessel so that it is distal of the side-branch vessel. Guide wire 56A, which until this point has remained within guide wire lumen 53A (see FIG. 8K), is advanced distally as depicted in FIG. 8L and advanced into the main vessel distally of the side-branch vessel. Guide wire 41A is then withdrawn proximally through guide wire lumen 58 until guide wire distal end 41B is able to exit guide wire lumen distal end 55B, as shown in FIG. 8L. Since guide wire lumen 55B is preformed and has bias, it will spring outwardly. Guide wire 41A can then be advanced into the side-branch vessel for further positioning. As the catheter 50 is advanced over the guide wires, distal portion 41B of the guide wire will push against the ostium of the side-branch vessel thereby insuring the location of main-vessel stent 20, and importantly aperture 25 will align with the opening to the side-branch vessel 5.

In order to assist in properly aligning main-vessel stent 20 in main-vessel 6, positioning guide wire lumen 55A, on main-vessel catheter 50, can be radiopaque, or have a radiopaque marker associated therewith so that it is visible under fluoroscopy. Thus, when advancing main-vessel catheter 50, the proper orientation can be more easily determined by viewing the position of positioning guide wire lumen 55A in connection with main-vessel 6. Additionally, positioning guide wire 56A for positioning main-vessel stent 20 is either radiopaque or has radiopaque portions, such as gold markers, to assist in positioning and orienting the catheter and stent during implantation and deployment.

While the foregoing description contemplates implanting a stent in side-branch vessel 5 prior to implanting main-vessel stent 20 in main-vessel 6, in an alternative embodiment, the implanting procedure can be reversed. However, it should be understood that by implanting main-vessel stent 20 in main-vessel 6, and subsequently implanting a stent in side-branch vessel 5, aperture 25 must be carefully aligned with side-branch vessel 5 so that side-branch catheter 31 can be advanced through expanded main-vessel stent 20 and aperture 25 and into side-branch vessel 5 for implanting the stent in side-branch vessel 5.

While main-vessel catheter 50 has been described herein as being of the rapid-exchange type, it also can be of a conventional over-the-wire-type catheter. In over-the-wire-type catheters, the guide wire lumen extends from the distal end of the catheter to the proximal end with no side port as is found in the rapid-exchange-type catheters. Typical of over-the-wire-type catheters is the type disclosed in U.S. Pat. Nos. 4,323,071 and B1 4,323,071, which are incorporated herein by reference, and are commonly assigned and commonly owned by Advanced Cardiovascular Systems, Inc., Santa Clara, Calif.

Figure 10:
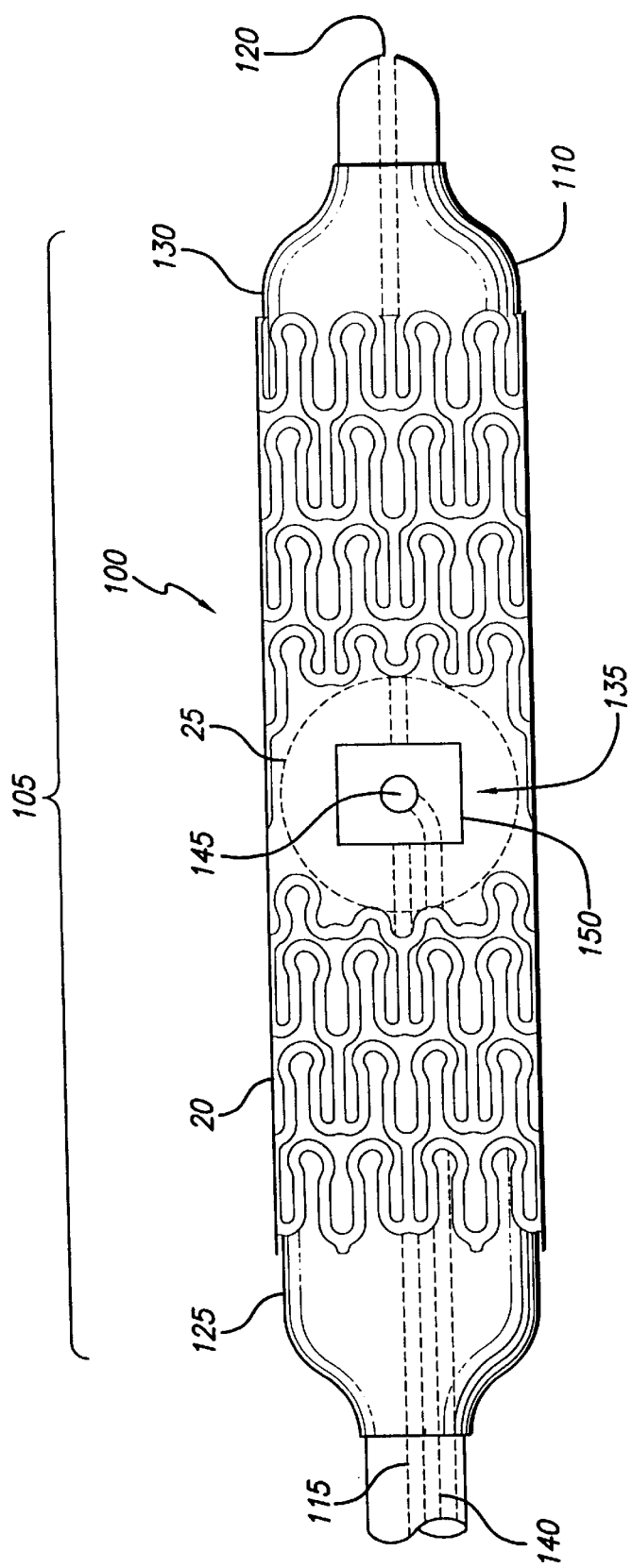
FIG. 10 is an elevation view, partially in section, of an alternative embodiment of the main-vessel catheter of FIGS. 8A–C having two expandable balloons separated by a section of catheter having an exit port for a stent-positioning guide wire.

In another embodiment of the invention, as depicted in FIG. 10, main-vessel stent 20 may be mounted on a main-vessel catheter 100. In this embodiment, main-vessel catheter 100 includes an expandable portion 105 located near distal end 110 of main-vessel catheter 100. Main-vessel catheter 100 includes guide wire lumen 115 which extends to port 120 located at distal end 110 of the main-vessel catheter. Expandable portion 105 includes a proximal balloon 125 and a distal balloon 130 separated by exit notch 135. Exit notch 135 is formed from the body of main-vessel catheter 100, and may have the same, a lesser or a greater diameter than the remainder of the catheter body. The main-vessel catheter 100 also has a stent-positioning guide wire lumen 140 that extends through the main-vessel catheter to exit port 145 located in exit notch 135.

Main-vessel catheter 100 may be configured as a so-called rapid-exchange catheter system which includes a slit (not shown) as is known in the art, and appropriate side ports for introduction of the guide wire and stent-positioning guide wire (not shown). Alternatively, main-vessel catheter 100 may be configured as an over-the-wire catheter system. Typically, proximal balloon 125 and distal balloon 130 are non-distensible balloons of the type known in the art for delivering and expanding stents.

Main-vessel stent 20 is mounted on expandable portion 105 of main-vessel catheter 100 by crimping stent 20 over proximal balloon 125 and distal balloon 130 and orienting stent 20 so that aperture 25 is positioned over exit port 145 in exit notch 135 of main-vessel catheter 100 to allow a stent-positioning guide wire to extend out of exit port 145, through aperture 25 and into the ostium of side-branch vessel 5. In one embodiment, exit notch 135 includes a marker band 150 to aid in positioning aperture 25 of main-vessel stent 20 in the desired location relative to the ostium of side-branch vessel 5.

The procedure for positioning and implanting main-vessel stent 20 using main-vessel catheter 100 is similar to the method described above with reference to FIGS. 8A–8C and 9A–9D. Expansion of stent 20, however, differs from the method described above since expandable portion 105 of main-vessel catheter 100 includes proximal balloon 125 and distal balloon 130 separated by exit notch 135. In this embodiment, after main-vessel stent 20 is located and properly situated at the site of the lesion in main-vessel 6 and the aperture 25 of main-vessel stent 20 is properly aligned with the ostium of side-branch vessel 5, proximal balloon 125 and distal balloon 130 are expanded either simultaneously or separately, depending on the physicians choice. After expansion, proximal balloon 125 and distal balloon 130 are deflated, and main-vessel catheter 100 is pulled back by the physician by pulling a portion of the catheter from the patient's body. Main-vessel catheter 100 is pulled back just sufficiently to position the distal balloon 130 in the center of stent 20 so that the portion of stent 20 originally positioned over exit notch 135 may be expanded. Once distal balloon 130 is properly positioned, it is expanded, thus completing the expansion of stent 20. Distal balloon 130 is then deflated, and main-vessel catheter 100 is withdrawn from the patient. As described previously, the design of main-catheter 100 allows both the main and stent-positioning guide wires to remain in the main-vessel and side-branch vessels in case further stent deployment or expansion are necessary.

While the invention herein has been illustrated and described in terms of an apparatus and method for stenting bifurcated vessels, it will be apparent to those skilled in the art that the stents and delivery systems herein can be used in the coronary arteries, veins and other arteries throughout the patient's vascular system. Certain dimensions and materials of manufacture have been described herein, and can be modified without departing from the spirit and scope of the invention.

What is claimed is:

1. A main-vessel stent for implanting in a main vessel adjacent a bifurcation, comprising:

a cylindrical member having a distal end and a proximal end and an outer wall surface therebetween; and a plurality of closed stent cells, at least some of the closed cells having a first perimeter and at least some of the closed cells having a second perimeter;

an aperture on the outer wall surface, the aperture having a third perimeter formed entirely of the closed stent cells, the third perimeter being different than either of the first perimeter and the second perimeter, the aperture being sized and positioned on the outer wall surface so that when the stent is implanted in a main vessel, the third aperture is aligned with a side-branch vessel thereby allowing substantially unrestricted blood flow from the main vessel through to the side-branch vessel.

2. The main-vessel stent of claim 1, wherein the stent is expandable from a first smaller diameter for delivery in a body lumen to a second expanded diameter by plastically deforming the stent beyond the elastic limits of the material forming the stent.

3. The main-vessel stent of claim 1, wherein the stent is formed from a self-expanding material so that the stent expands from a first smaller diameter for delivery through a body lumen to a second implanted diameter in the body lumen.

4. The main-vessel stent of claim 1, wherein the cylindrical member further comprises:

a distal region adjacent the distal end, a proximal region adjacent the proximal end and a central region located therebetween; and wherein the aperture is formed in the central region.

5. The main-vessel stent of claim 4, wherein the stent cells of the distal and proximal regions have a first cell size and the stent cells of the central region have a second cell size.

6. The main-vessel stent of claim 5, wherein the second cell size is less than the first cell size.

7. The main-vessel stent of claim 6, wherein the second cell size is about one half the size of the first cell size.

* * * * *

UNITED STATES PATENT AND TRADEMARK OFFICE
CERTIFICATE OF CORRECTION

PATENT NO.     : 6,582,394 B1
DATED          : June 24, 2003
INVENTOR(S)    : Paul Reiss and Mary Dennehy It is certified that error appears in the above-identified patent and that said Letters Patent is hereby corrected as shown below:

<u>Column 14,</u>
Line 2, delete "third".

Signed and Sealed this

Thirteenth Day of April, 2004

JON W. DUDAS
*Acting Director of the United States Patent and Trademark Office*